United States Patent [19] [11] 4,005,118
Heckert et al. [45] Jan. 25, 1977

[54] ORGANOSILANE COMPOUNDS

[75] Inventors: David C. Heckert, Oxford; David M. Watt, Jr., Cincinnati, both of Ohio

[73] Assignee: The Procter & Gamble Company, Cincinnati, Ohio

[22] Filed: Apr. 22, 1975

[21] Appl. No.: 570,532

[52] U.S. Cl. ............... 260/448.8 R; 260/448.2 N; 252/546; 428/543
[51] Int. Cl.² ............... C07F 7/10; C07F 7/18
[58] Field of Search ............... 260/448.2 N, 448.8 R

[56] References Cited
UNITED STATES PATENTS

| | | | |
|---|---|---|---|
| 2,972,598 | 2/1961 | Morehouse | 260/448.8 R X |
| 3,389,160 | 6/1968 | Reid | 260/448.2 N |
| 3,471,541 | 10/1969 | Morehouse | 260/448.2 N X |
| 3,557,178 | 1/1971 | Golitz et al. | 260/448.8 R |
| 3,580,920 | 5/1971 | Culpepper | 260/448.8 R X |
| 3,624,120 | 11/1971 | Yetter | 260/448.2 N |
| 3,658,867 | 4/1972 | Prokai | 260/448.2 N |
| 3,661,963 | 5/1972 | Pepe et al. | 260/448.2 N |
| 3,817,739 | 6/1974 | Abbott et al. | 260/448.8 R X |
| 3,836,559 | 9/1974 | Prokai | 260/448.2 N |
| 3,898,257 | 8/1975 | Gregory | 260/448.8 R |

Primary Examiner—Paul F. Shaver
Attorney, Agent, or Firm—C. R. Wilson; R. B. Aylor; T. H. O'Flaherty

[57] ABSTRACT

Novel compounds of formula

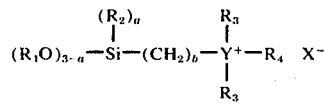

or siloxane oligomers thereof, wherein $R_1$ is an alkyl group containing 1 to 4 carbon atoms; $a$ is 0 to 2; $R_2$ is an alkyl group containing 1 to 18 carbon atoms; $b$ is 1 to 3; at least one $R_3$ is a carboxy-substituted alkyl group containing 1 to 4 carbon atoms or

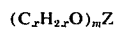

wherein $x$ is 2 to 4, $m$ is 1 to 20, Z is hydrogen, an alkyl group containing 1 to 18 carbon atoms or an acyl group containing 1 to 4 carbon atoms provided $m$ is greater than 1 when Z is hydrogen, while the other $R_3$ is an alkyl, aryl or arylalkyl group containing 1 to 12 carbon atoms; $R_4$ is an alkyl, aryl, or arylalkyl group containing 1 to 22 carbon atoms; X is halide; and Y is nitrogen, phosphorus, or sulfur are disclosed. The novel compounds are useful for inclusion in a detergent composition for imparting soil release benefits to metallic and vitreous surfaces washed or rinsed therewith.

11 Claims, No Drawings

ORGANOSILANE COMPOUNDS

BACKGROUND OF THE INVENTION

This invention relates to novel organosilane compounds.

Various quaternized substituted organosilane compounds are known. For example, British Pat. No. 686,068 discloses compounds having the general formula

where R is an alkyl, monocyclic aryl hydrocarbon or alkoxy radical, $R^1$ is an alkyl, alicyclic hydrocarbon or monocyclic aryl hydrocarbon radical or hydroxy alkyl radical, $a$ is 1 to 2, $b$ is 0 to 3 with $a+b$ being not greater than 4 and Y is an acid anion. British Pat. No. 1,164,581 discloses compounds of the general formula

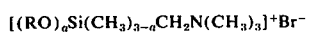

wherein R is an alkyl radical containing 1 to 6 carbon atoms or a phenyl radical and $a$ is 1 or 2. U.S. Pat. No. 3,730,701 discloses compounds of the formula

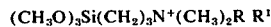

wherein R is an alkyl radical having 11 to 22 carbon atoms and $R^1$ is a halide.

British Pat. No. 882,067 discloses compounds of formula

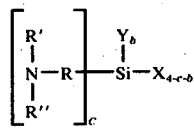

wherein R is a substituted or unsubstituted alkyl group, R' and R'' are hydrogen, or organic radicals, preferably alkyl, aminoalkyl, cyanoalkyl, hydroxyalkyl, carboalkoxyalkyl, carboxyalkyl or aryl radicals, or the monovalent grouping

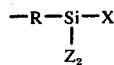

X is an alkoxy radical or the oxygen atom of a siloxylidyne radical    Si — O —, or R' and R'' together with the nitrogen atom may form a heterocyclic ring, Y is a hydroxy, alkoxy, alkyl or aryl radical, Z is an alkoxy, alkyl, or aryl radical, $c$ is 1 or 2, $b$ is 0 to 2, and $c+b$ is not more than 3.

Compounds of formula

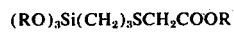

where R and R' are lower monovalent alkyl radicals are disclosed in U.S. Pat. No. 2,563,516.

It has now been found that novel compounds as hereindescribed are useful as an additive to a detergent composition. Commonly assigned copending patent applications "Organosilane-Containing Detergent Composition" and "Organosilane-Containing Anionic Detergent Compositions," both by Heckert and Watt, filed of even date (P&G Cases 2208 and 2209, respectively) disclose detergent compositions containing a class of organosilanes. When metallic or vitreous surfaces are washed with a detergent composition containing the organosilane, a thin polymeric coating of the organosilane is deposited upon the washed or rinsed surfaces. The polymerized coating imparts a soil release benefit to the surface, thereby making the surface easier to clean in subsequent washings.

It is an object of this invention to produce novel organosilane compounds.

It is another object of this invention to produce organosilane compounds having utility in a detergent composition.

These and other objects will become apparent from the description to follow.

As used herein all percentages and ratios are by weight unless otherwise indicated.

SUMMARY OF THE INVENTION

An organosilane having the formula

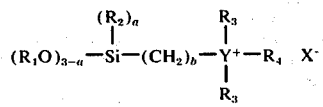

or siloxane oligomers thereof, wherein $R_1$ is an alkyl group containing 1 to 4 carbon atoms; $a$ is 0 to 2; $R_2$ is an alkyl group containing 1 to 18 carbon atoms; $b$ is 1 to 3; at least one $R_3$ is a carboxy-substituted alkyl group containing 1 to 4 carbon atoms or

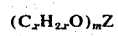

wherein $x$ is 2 to 4, $m$ is 1 to 20, Z is hydrogen, an alkyl group containing 1 to 18 carbon atoms or an acyl group containing 1 to 4 carbon atoms provided $m$ is greater than 1 when Z is hydrogen, while the other $R_3$, if any, is an alkyl, aryl or arylalkyl group containing 1 to 12 carbon atoms; $R_4$ is an alkyl, aryl, or arylalkyl group containing 1 to 22 carbon atoms; X is halide; and Y is nitrogen, phosphorus, or sulfur.

DETAILED DESCRIPTION OF THE INVENTION

This invention relates to organosilane compounds having the formula

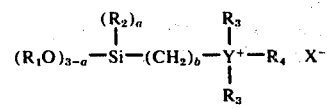

or siloxane oligomers thereof wherein $R_1$, $a$, $R_2$, $b$, $R_3$, $R_4$, Y and X are as defined immediately above. Preferably X is chloride or bromide, $a$ is 0 or 1, $R_3$ is a carboxy-substituted alkyl group and $R_4$ is an alkyl, aryl or arylalkyl group containing 6 to 12 carbon atoms.

It should be understood that $R_3$ in the above formula and formulas to follow may be the same or different. When one $R_3$ is an aryl or arylalkyl group, it contains 6 to 12 carbon atoms. It should be further understood that when Y is sulfur, there will be only one $R_3$. The 1 to 4 carbon atoms in the carboxy-substituted alkyl group is inclusive of the carboxyl group. Under basic conditions, when $R_3$ is the anion of a carboxylic substituted alkyl, the counter ion $X^-$ is not extant.

Compounds of formula $$(R_1O)_3-Si-(CH_2)_b-\underset{R_3}{\overset{R_3}{\underset{|}{\overset{|}{Y^+}}}}-R_4 \; X^- \qquad I.$$

wherein $b$ is 3, $R_3$ is a carboxy-substituted alkyl group, and $R_1$, $R_4$, $Y$ and $X$ are defined as above are prepared by the following route:

$X_3SiH$ + $CH_2=CHCH_2X$ ⟶ $X_3Si(CH_2)_3X$
(trihalosilane) (allyl halide) (gamma-halopropyltrihalosilane)

$X_3Si(CH_2)_3X$ + $3R_1OH$ ⟶ $(R_1O)_3Si(CH_2)_3X$ + $3HX$
(alcohol) (gamma-halopropyltrialkoxysilane)

$(R_1O)_3Si(CH_2)_3X$ + $(R_3)_{1-2}YR_4$ ⟶ $(R_1O)_3Si(CH_2)_3\underset{R_3}{\overset{R_3}{\underset{|}{\overset{|}{Y^+}}}}-R_4 \; X^-$ (tertiary amine, tertiary phosphine, or dialkylsulfide having carboxy-substituted alkyl groups) (gamma-trialkylammoniopropyltrialkoxysilane halide gamma-trialkylphosphoniopropyltrialkoxysilane halide, or gamma-dialkylsulfoniopropyltrialkoxysilane halide)

The trihalosilane (where the halogen is chlorine or bromine) is reacted with the allyl chloride at about 100° C. for from 4 to 10 hours in the presence of a catalyst, e.g., chloroplatinic acid or platinum. The resultant gamma-halopropyltrihalosilane is reacted with a lower alcohol to product the gamma-halopropyltrialkoxysilane. At least three equivalents of alcohol per equivalent of halopropyltrihalosilane are added slowly to the silane. The gamma-halopropyltrihalosilane may be dissolved in an inert solvent, preferably hexane or pentane. (See W. Noll, "Chemistry and Technology of Silanes," Academic Press, New York, 1968, page 81 for the alcoholysis of halosilanes.) One equivalent of the gamma-halopropyltrialkoxysilane is reacted with one equivalent of the carboxyl-containing tertiary amine, tertiary phosphine, or dialkylsulfide to produce the organosilane. An inert solvent, preferably of high dielectric constant, may be used. The reaction is carried out at temperatures of from 50° to 200° C. and a time of 2 to 20 hours for the reaction of the halidepropyltrialkoxysilane.

Such carboxy-substituted tertiary amines, tertiary phosphines, and dialkylsulfides are produced by reacting $R_3YHR_4$ or $HYR_4$ (where Y is sulfur)

with $X(CH_2)_{1-3}COOH$ in the presence of base at elevated temperatures, e.g., 50° to 150° C.

The compounds of Formula I when at least one $R_3$ is $(C_xH_{2x}O)_mZ$ with $x$, $m$ and $Z$ as defined above are produced in the manner given above except for the last reaction step. Thus, alpha-beta- and gamma-haloalkyltrialkoxysilane is reacted with a tertiary amine, tertiary phosphine, or dialkylsulfide where at least one substituent is $(C_xH_{2x}O)_mZ$ The reaction takes place at a temperature of 50° to 200° C. and a time of from 2 to 10 hours.

When $b$ is 2 in Formula I, a trihalovinylsilane of formula $X_3SiCH=CH_2$ (which is commercially available) is reacted with hydrogen bromide in the presence of peroxide and light to produce a beta-haloethyltrihalosilane. This compound is reacted with an alcohol and thereafter with an appropriate amine, phosphine, or sulfide in the manner discussed above for the preparation of the compounds of Formula I when $b$ is 3.

When $b$ is 1 in Formula I, the starting reactant is a commercially available trihalomethylsilane of formula $X_3SiCH_3$.

This silane is reacted with chlorine or, preferably a half mole of bromine and a half mole of chlorine in the presence of light (such as provided by an ordinary tungsten or fluorescent lamp). The resultant alphahalomethyltrihalosilane is reacted with an alcohol and thereafter an appropriate amine, phosphine or sulfide in the manner discussed above with the compounds of Formula I when $b$ is 3.

Compounds of Formula I where one $R_3$ is an alkyl, aryl or arylalkyl group, are produced by using an appropriate amine, phosphine or sulfide in the last reaction step.

Examples of compounds illustrative of compounds of Formula I follow:

$(CH_3O)_3SiCH_2N^+(C_2H_4COOH)_2C_{10}H_{21}$ $Br^-$
$(C_2H_5O)_3Si(CH_2)_3N^+(CH_2COOH)(CH_3)C_6H_5$ $Cl^-$
$(C_2H_5O)_3Si(CH_2)_2P^+(C_3H_6COOH)(C_2H_5)C_{10}H_{21}$ $Cl^-$
$(C_4H_9O)_3SiCH_2S^+(C_2H_4COOH)C_6H_{13}$ $Br^-$
$(CH_3O)_3SiCH_2N^+[(C_2H_4O)_3H](CH_3)C_8H_{17}$ $Cl^-$
$(C_2H_5O)_3Si(CH_2)_3N^+[(C_2H_4O)_6H]_2C_{10}H_{21}$ $Cl^-$
$(CH_3O)_3SiCH_2N^+[(C_2H_4O)_3COCH_3]_2C_8H_{17}$ $Cl^-$
$(C_3H_7O)_3SiCH \; P^+[(C_3H_6O)_{12}H]_2CH_2C_6H_5$ $Cl^-$
$(C_4H_9O)_3Si(CH_2)_3P^+](C_2H_4O)_4C_4H_9]CH_3C_4H_9$ $Br^-$
$(CH_3O)_3Si(CH_2)_2P^+[(C_2H_4O)_5COC_2H_5]_2C_4H_9$ $Br^-$
$(CH_3O)_3SiCH_2S^+](C_2H_4O)_5H]C_{10}H_{21}$ $Cl^-$
$(C_2H_5O)_3Si(CH_2)_2S^+[(C_3H_6O)_8C_3H_7]C_4H_9$ $Br^-$
$(CH_3O)_3Si(CH_2)_3S^+[(C_2H_4O)_{12}COC_4H_9]C_{12}H_{25}$ $Cl^-$
$(CH_3O)_3Si(CH_2)_2N^+[(C_4H_8O)_{15}CH_3](CH_3)C_6H_{13}$

Compounds of formula

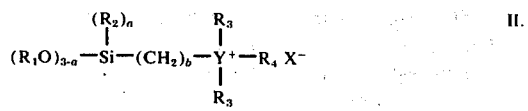

wherein $R_1$, $R_2$, b, $R_3$, $R_4$, Y and X are as defined above and a is 1 or 2 are prepared in a manner similar to the preparation of the compounds of Formula I except for the fact that the starting reactants (when b is 1, 2, or 3) all have a $C_{1-18}$ alkyl group or two $C_{1-18}$ alkyl groups attached to the Si atom in place of a halogen atom(s). The starting reactant is commercially available when $R_2$ is $CH_3$. When $R_2$ is $C_2H_5$ or greater, the compound is prepared by reacting a silane with an appropriate olefin. Thus, $$X_{3-a}SiH_{1+a}$$

is reacted with a $C_2$ to $C_{18}$ olefin to obtain the desired starting reactant. The remaining reaction steps and conditions for producing the desired organosilane of Formula II are essentially the same as for producing the compounds of Formula I.

Examples of compounds of Formula II are:

$(CH_3O)_2C_{16}H_{33}Si(CH_2)_3N^+(C_2H_4COOH)(CH_3)C_4H_9$ $Cl^-$
$(C_2H_5O)(CH_3)_2Si(CH_2)_2P^+(CH_2COOH)_2C_{10}H_{21}$ $Cl^-$
$(C_3H_7O)_2CH_3SiCH_2S^+(C_3H_6COOH)C_6H_{13}$ $Cl^-$
$(CH_3O)_2CH_3SiCH_2N^+[(C_3H_6O)_{20}H]_2C_6H_5$ $Cl^-$
$(CH_3O)_2C_2H_5Si(CH_2)_2N^+[(C_4H_8O)_6C_2H_5]_2CH_3$ $Cl^-$
$(C_2H_5O)(CH_3)_2SiCH_2P^+[(C_2H_4O)_2H](CH_2C_6H_5)_2$ $Cl^-$
$(C_2H_5O)_2C_8H_{17}Si(CH_2)_3P^+[(C_2H_4O)_4C_6H_{13}]_2C_4H_9$ $Cl^-$
$(CH_3O)_2CH_3SiCH_2P^+[(C_2H_4O)_6COCH_3]_2C_8H_{17}$ $Cl^-$
$(CH_3O)_2CH_3SiCH_2S^+[(C_3H_6O)_2H]C_{14}H_{29}$ $Cl^-$
$(C_2H_5O)(C_2H_5)_2Si(CH_2)_3S^+[(C_2H_4O)_5CH_3]C_8H_{17}$ $Br^-$
$(C_2H_5O)_2C_{10}H_{21}SiCH_2N^+[(C_2H_4O)_2COC_2H_5](C_4H_9)_2$ $Cl^-$
$(CH_3O)_2C_4H_9Si(CH_2)_2S^+[(C_2H_4O)_2COCH_3]C_{12}H_{25}$ $Br^-$

Siloxane oligomers of the organosilanes are formed from the monomers by the controlled addition of from 1 to 100 equivalents of water, preferably in an inert solvent such as alcohol, tetrahydrofuran, etc. As used herein, "oligomers" is used to mean a degree of polymerization of from 2 to 100, preferably 2 to 20. A higher degree of polymerization adversely affects the ability of the compound to bond itself to a metallic or vitreous surface as discussed below and is for this reason avoided. Examples of siloxane oligomers having varying degrees of polymerization are readily visualized from the above examples of organosilane monomers.

The above organosilanes are useful when used in a detergent composition at a level of organosilane to water-soluble organic detergent of from 2:1 to 1:10,000. When metallic or vitreous surfaces are washed or rinsed with a detergent composition containing the above described organosilane, a soil release benefit is imparted to the surface. It is theorized that the positively charged organosilane is attracted to the negatively charged surface. The silicon atom in the organosilane can then form a bond with the surface. The presence of the positive charge on the organosilane is necessary to allow the bonding to take place from a dilute solution as is normally encountered with detergent compositions and within a reasonable time period. The terminal alkyl groups attached to the positively charged atom provides the soil release benefits. It is believed that the organosilane compound polymerizes on the surface to form a thin coating of the polymer. The coating is responsible for imparting the soil release benefits to the surface. That is, a hard surface having on it the polymeric coating will be soiled; however, the soil is not tenaciously bound to the surface by virtue of the coating and for this reason is easily washed away.

The following examples are illustrative of the invention.

EXAMPLE I $(CH_3O)_3Si(CH_2)_3N^+(CH_3)(CH_2CH_2COOH)C_8H_{17}$ $Br^-$

A mixture of 19.9 grams of gamma-chloropropyltrimethoxysilane (commercially available) and 14.3 gm. of octylmethylamine is heated to 100°–120° C. for 16 hours. NMR indicated complete quaternization of the amine. To this mixture is added 0.1 mole of sodium methoxide in 50 ml. of methanol. After stirring for 6 hours the methanol is removed under vacuum and the residue is dissolved in cold hexane and filtered to yield gamma-octylmethylaminopropyltrimethoxysilane. To this product is added 0.1 mole of sodium beta-bromopropionate in 300 ml. of methanol. The mixture is warmed gently for 6 hours, then refluxed for an additional 6 hours to yield the desired quaternary ammonium salt.

Substitution of octylmethylphosphine or methylsulfide for the octylmethylamine in the above sequence of steps leads to corresponding phosphorous- and sulfur-containing organosilanes.

EXAMPLE II $(CH_3O)_3SiCH_2N^+(CH_3)[(CH_2CH_2O)_{5.5}H]C_{12}H_{25}$ $Cl^-$

Chloromethyltrimethoxysilane (16.8g) and 63.9g of ethoxylated dodecylmethylamine (average ethoxylate level 5.5) are heated without solvent to 120° C. for 20 hours to yield the desired quaternary ammoniosilane.

EXAMPLE III $(CH_3O)_2(CH_3)SiCH_2N^+(CH_3)(CH_2COO^-)CH_2C_6H_5$

Two moles of dimethyldichlorosilane are brominated with a mixture of 0.5 moles of bromine and 0.5 moles of chlorine in a pyrex chamber irradiated by an ordinary 150 watt tungsten floodlight. After the bromine color has completely disappeared, the residue is distilled to yield 0.9 moles of bromomethylmethyldichlorosilane. To this is added with rapid stirring and a fast nitrogen flush, 2 moles of dry methanol. After all HCl evolution has ceased, the product is distilled to yield bromomethylmethyldimethoxysilane.

To 0.25 moles of bromomethylmethyldimethoxysilane is added 0.25 moles of methylbenzylamine, and the mixture is heated to 100° C. for 12 hours. At the end of that time, 300 ml of hexane is added and excess trimethylamine is added. This mixture is allowed to stir for 3 hours, filtered, and the hexane is removed under reduced pressure, leaving benzylmethylaminomethylmethyldimethoxysilane.

To 23.9g. (0.1 mole) of benzylmethylaminomethylmethyldimethoxysilane is added 17.5g (0.1 mole) of sodium beta-bromopropionate in 200 ml. of ethanol.

The resulting mixture is refluxed with stirring for 12 hours until NMR spectra show complete quaternization of the amine.

What is claimed is:

1. An organosilane having the formula

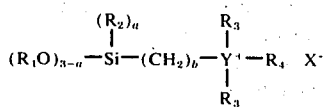

or siloxane oligomers thereof, wherein $R_1$ is an alkyl group containing 1 to 4 carbon atoms; $a$ is 0 to 2; $R_2$ is an alkyl group containing 1 to 18 carbon atoms; $b$ is 1 to 3; at least one $R_3$ is a carboxy-substituted alkyl group containing 1 to 4 carbon atoms or

wherein $x$ is 2 to 4, $m$ is 1 to 20, Z is hydrogen, an alkyl group containing 1 to 18 carbon atoms, or an acyl group containing 1 to 4 carbon atoms provided $m$ is greater than 1 when Z is hydrogen, while the other $R_3$ is an alkyl, aryl or arylalkyl group containing 1 to 12 carbon atoms; $R_4$ is an alkyl, aryl or arylalkyl group containing 1 to 22 carbon atoms; X is halide; and Y is nitrogen, phosphorus or sulfur.

2. The organosilane of claim 1 wherein $a$ is 0 or 1.
3. The organosilane of claim 1 wherein $a$ is 2.
4. The organosilane of claim 1 wherein $R_3$ is a carboxy-substituted alkyl group.
5. The organosilane of claim 1 wherein $R_3$ is $(C_xH_{2x}O)_mZ$.
6. The organosilane of claim 1 wherein the siloxane oligomer has a degree of polymerization of from 2 to 100.
7. The organosilane of claim 6 wherein the degree of polymerization is from 2 to 20.
8. The organosilane of claim 1 wherein the organosilane is a monomer.
9. The organosilane of claim 1 wherein X is chloride or bromide.
10. The organosilane of claim 1 wherein $R_4$ contains 6 to 12 carbon atoms.
11. The organosilane of claim 1 having the formula

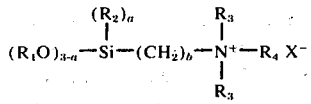

or siloxane oligomers thereof, wherein $R_1$ is an alkyl group containing 1 to 4 carbon atoms; $a$ is 0 to 2; $R_2$ is an alkyl group containing 1 to 18 carbon atoms; $b$ is 1 to 3; at least one $R_3$ is a carboxy-substituted alkyl group containing 1 to 4 carbon atoms or

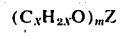

wherein $x$ is 2 to 4, $m$ is 1 to 20, Z is hydrogen, an alkyl group containing 1 to 18 carbon atoms, or an acyl group containing 1 to 4 carbon atoms provided $m$ is greater than 1 when Z is hydrogen, while the other $R_3$ is an alkyl, aryl or arylalkyl group containing 1 to 12 carbon atoms; $R_4$ is an alkyl, aryl or arylalkyl group containing 1 to 22 carbon atoms; and X is halide.

* * * * *